United States Patent [19]

Pedjac

[11] Patent Number: 4,521,633

[45] Date of Patent: Jun. 4, 1985

[54] BROMINATION PROCESS

[75] Inventor: Joseph J. Pedjac, Mt. Pleasant, Mich.

[73] Assignee: The Dow Chemical Company, Midland, Mich.

[21] Appl. No.: 496,037

[22] Filed: May 19, 1983

[51] Int. Cl.$^3$ .............................................. C07C 41/22
[52] U.S. Cl. .................................................... 568/639
[58] Field of Search ........................................ 568/639

[56] References Cited

U.S. PATENT DOCUMENTS

| | | |
|---|---|---|
| 2,022,634 | 11/1935 | Britton et al. . |
| 3,232,959 | 2/1966 | Hahn . |
| 3,285,965 | 11/1966 | Jenkner . |
| 3,366,694 | 1/1968 | Thompson . |
| 3,733,366 | 5/1973 | Burk . |
| 3,752,856 | 8/1973 | Nagy et al. . |
| 3,833,674 | 9/1974 | Brackenridge ...................... 568/639 |
| 3,845,146 | 10/1974 | Moore et al. . |
| 3,959,387 | 5/1976 | Brackenridge . |
| 3,965,197 | 6/1976 | Stepniczka . |
| 4,287,373 | 9/1981 | Garman et al. ..................... 568/639 |
| 4,327,227 | 4/1982 | Ayres et al. ........................ 568/639 |

FOREIGN PATENT DOCUMENTS

| | | |
|---|---|---|
| 981833 | 1/1965 | United Kingdom . |
| 1411524 | 10/1975 | United Kingdom . |
| 2081253A | 2/1982 | United Kingdom . |

OTHER PUBLICATIONS

Cook, N. A., "Phenyl Ether and Some of Its Derivatives", 32, *J.A.C.S.* 1285, (1910).

Primary Examiner—Bernard Helfin
Attorney, Agent, or Firm—Paul D. Hayhurst

[57] ABSTRACT

Prepare high purity perbrominated aromatic compounds, especially decabromodiphenyl oxide, by adding an aromatic compound to a mixture comprising an organic solvent, a catalyst, and a slight stoichiometric excess of bromine, at a low initial reaction temperature.

17 Claims, No Drawings

BROMINATION PROCESS

BACKGROUND OF THE INVENTION

This invention relates to the preparation of brominated aromatic compounds. More specifically, it pertains to a process for the perbromination of aromatic compounds.

High levels of purity are required for brominated aromatic compounds which have found utility as flame retardant agents in polymer compositions. In particular, it is important that such brominated products have extremely low levels of residual impurities such as free bromine, hydrogen bromide, retained catalysts, by-product bromine-containing derivatives and the like since the presence of such impurities can have undesirable effects on the polymer compositions in which such agents are used. Purity is particularly important from the standpoint of color.

High purity is an especially important consideration in the case of decabromodiphenyl ether, a flame retardant agent that has found wide application as an additive for high impact polystyrene used in television cabinets and other consumer appliances.

Known methods for the perbromination of diphenyl ether include, for example, methods described in U.S. Pat. Nos. 2,022,634; 3,232,959; 3,752,856; 3,833,674; and 3,959,387. Thus, while there are several known methods for the production of decabromodiphenyl ether, the vast majority of these methods are incapable of producing decabromodiphenyl ether having an assay above 95 percent. This problem is compounded by the fact that traditional purification methods, such as recrystallization techniques, are usable only with difficulty with decabromodiphenyl ether because its limited solubility in available solvents makes recrystallization both cumbersome and uneconomical.

It is noted that U.S. Pat. No. 4,287,373 discloses a method capable of producing decabromodiphenyl oxide in assays of greater than 95 percent. Said patent teaches a process for perbrominating aromatics, such as phenol or diphenyl ether by adding the aromatic to a large excess of $Br_2$ at a temperature of from 35° C. to 55° C., and then finishing the reaction at an elevated temperature at which reflux can occur. The use of such high excesses of bromine is disadvantageous in many ways. For example, the use of excess bromine as a reaction solvent gives products which contain undesirably large amounts of occluded free bromine.

In view of the deficiencies of prior art perbromination methods, it would be desirable to have a process for the perbromination of aromatic compounds which would produce highly pure perbrominated products in high yield by a relatively simple reaction, and which could be operated without requiring large excesses of bromine.

SUMMARY OF THE INVENTION

The present invention is such a process for the preparation of highly pure perbrominated aromatic compounds in high yield. More specifically, the present invention is a process for preparing perbrominated aromatic compounds by adding an aromatic compound to a brominating agent in an organic solvent in the presence of a catalyst at a temperature of about 15° C. or lower, and then raising the temperature of the resulting reaction mixture to an elevated temperature in order to achieve substantial perbromination of the aromatic compound.

Advantageously, the process of the present invention proceeds readily at low addition temperatures to yield a high purity perbrominated product. Surprisingly, the process of the present invention is capable of producing decabromodiphenyl oxide having an assay higher than 95 percent. The process has the further advantage of requiring only a slight stoichiometric excess of bromine. Perbrominated aromatic compounds generally are useful as flame retardants for plastics and other organic materials.

DETAILED DESCRIPTION OF THE INVENTION

The present invention is a process for perbrominating aromatic compounds. Diphenyl oxide is the preferred aromatic compound. It should be noted that the aromatic compounds suitable for use in the process of the present invention include nonbrominated aromatic compounds as well as partially brominated aromatic compounds and mixtures thereof.

A brominating agent is employed in the practice of the present invention. While it may be possible to employ known brominating agents which are useful for the bromination of aromatic rings, bromine is the preferred brominating agent when high purity products are desired. In contrast to prior art processes for the high yield production of high purity perbrominated aromatic compounds, the process of the present invention requires only slight stoichiometric excesses of bromine. Typically, a stoichiometric excess of bromine ranging from about 0 to about 25 percent or more is employed. Preferably, a stoichiometric excess ranging from about 5 to about 15 percent is employed. Similarly, if a brominating agent is employed which is not bromine, the amount of said agent to be employed should provide bromine in the quantities stated hereinabove.

A catalyst is advantageously employed in the process of the present invention. Catalysts for the perbromination of aromatic compounds are well-known. See, e.g., U.S. Pat. No. 4,287,373, the teachings of which, with respect to species of bromination catalysts, are incorporated herein by reference. It should be noted that certain catalytic metals, such as aluminum, react violently with bromine, and care should be taken to avoid uncontrolled reactions between bromine and such metals. Preferred catalysts include aluminum bromine and aluminum chloride, with aluminum chloride being most preferred. The catalyst is employed in catalytic quantities. Preferably, the amount of catalyst employed ranges from about 0.1 to about 5 weight percent of catalyst based on the mass of aromatic compound employed. Larger amounts of catalyst may be employed, but may be economically impractical.

The catalyst may be employed in a variety of forms. When employing a non-metal catalyst, such as $AlCl_3$, a solid, homogeneous "lump" form is preferred. For the purposes of the present invention, lumps of non-metal catalyst may be crystalline or amorphous in varying degrees and may contain inert impurities which are not deleterious to the process of the present invention. Preferably, the lump form catalyst has a mean diameter which is from about ¼ to about 1 inch.

An organic solvent is employed to advantage in the process of the present invention. The solvent functions to solubilize the reactants and reaction products, and to aid in heat transfer. While the amount of solvent employed may range widely, the amount of solvent to be employed generally is indicated by practical considerations, and typically ranges from about 8 to about 20 moles of solvent per mole of aromatic compound. Preferably, from about 10 to about 15 moles of solvent are employed per mole of aromatic compound. Typical solvents include the perhalogenated lower alkyls. However, it is to be noted that methylene chloride is the preferred solvent due to its physical properties. The use of methylene chloride is particularly advantageous in that it exhibits very low susceptibility to transhalogenation at the low addition temperature employed in the process of the present invention.

According to the process of the present invention, an aromatic compound is slowly added to a mixture comprising an organic solvent, a catalyst, and bromine. When the addition of the aromatic compound is completed, the resulting reaction mixture typically is brought to elevated temperature until the reaction is completed and substantial perbromination of the aromatic compound is achieved. For the purposes of the present invention, the term "substantial perbromination" means that at least about 95 area percent, as determined by liquid chromatographic means, of the aromatic substrate which is to be brominated is converted to the fully brominated (perbrominated) state.

The addition temperature, i.e., the temperature of the reaction mixture during the period of addition of the aromatic compound thereto, typically is about 15° C. or lower. Preferably, the addition temperature is about 10° C. or less. Most preferably, the addition temperature is from about 5° C. to about −15° C.

The low addition temperature of the process of the present invention is advantageous in that it allows the production of high purity perbrominated aromatic compounds. The process of the present invention is additionally advantageous in that the problem of transhalogenation of the organic solvent is reduced by employing a low addition temperature. As mentioned hereinbefore, the potential for transhalogenation is further reduced by the use of methylene chloride as the organic solvent.

When the addition of the aromatic compound to the reaction mixture is completed, the total reaction mixture may be heated to elevated temperature in order to assure complete bromination. Typically, the total reaction mixture is heated to reflux temperature and said temperature is maintained until the reaction is complete. Completion of the reaction may be observed by following the rate of evolution of hydrogen bromide from the reaction mixture, i.e., the reaction is complete when the rate of hydrogen bromide evolution falls to zero. Ordinarily, the reaction will proceed at atmospheric pressure or higher, but subatmospheric pressure may be employed if desired.

A total reaction time of from 1 to 100 hours, dependent primarily on the aromatic reactant, is generally adequate for complete reaction under the conditions of the invention to convert quantitatively the starting materials to perbrominated products in which substantially all replaceable nuclear hydrogen atoms of the aromatic compound have been replaced by bromine. Typically, a total reaction time of up to about 20 hours will be sufficient to produce high yields of high assay products. In some cases, perbromination may be complete in three hours or less. It is desirable to add the aromatic compound to the reaction mixture at a sufficiently slow rate to minimize loss of bromine and solvent overhead and to permit the desired low reaction temperature to be maintained under conditions of control and safety.

Typically, the reaction system is maintained under anhydrous conditions until such time as the reaction is complete. Optionally, depending on the process conditions and related practical considerations, such as total reaction time, water may be added to the reaction system to prevent further reaction. Water has a detrimental effect upon the reaction, as it interferes with the operation of the catalyst.

When the reactants, catalyst and solvent are properly combined under reaction conditions as specified hereinbefore, a highly pure perbrominated aromatic compound will be formed in high yield.

The reaction mixture resulting from carrying out the process of the invention at low initial reaction temperature can be processed by a variety of known work-up procedures to isolate the perbrominated products. The crude reaction mixture, which may contain the brominated products, excess solvent and excess catalyst, can, for instance, be subjected to stripping either at atmospheric pressure or preferably under reduced pressure to the point of constant weight of the residue. The crude product which is thus isolated may be further purified, for instance, by digestion with methanol, ethylene dibromide, or dilute hydrochloric acid. This isolation method by stripping is fast, simple and gives reliable yield data and relatively pure product. It is preferred to employ a work-up method which neutralizes bromine as does, for example, the method employed in Example 1.

It is generally possible to predict the product(s) which will result from application of this perbromination process under optimum reaction conditions to any particular starting material. The general rule is that every nuclear hydrogen atom of the aromatic compound will be replaced by a bromine atom if the reaction is carried to completion, that is, until the evolution of hydrogen bromide has stopped. This level of bromination may be reached by proper adjustment of reaction temperature, catalyst concentration and reaction time. The perbromination process is continued until such time as the sampling indicates that the desired degree of bromination has been reached, or the bromination reaction may be continued until evolution of hydrogen bromide has substantially ceased. Extension of reaction periods beyond the desired point of bromination serves no useful purpose.

SPECIFIC EMBODIMENTS

The following example is given to illustrate the invention and should not be construed as limiting its scope.

EXAMPLE 1

To a 1-liter vessel are added 300 ml of methylene chloride, 3 g of lump-form $AlCl_3$ and 828 g of bromine. This represents approximately a 10 percent excess of bromine over the stoichiometric amount. The mixture is cooled to 5° C. with stirring. Then, 80 g of diphenyl oxide is dissolved in 60 ml of methylene chloride. Over a 3-hour period the solution of diphenyl oxide in methylene chloride is slowly added to the reaction vessel. The temperature of the contents of the vessel is maintained at from 5° C. to 6° C. during the period of addition. After the diphenyl oxide solution is completely added to the vessel, the temperature of the contents of the vessel is raised to 40°–41° C. and is held at reflux for 6.5 hours. Then, 200 ml of water is added to deactivate the catalyst, and the excess bromine is neutralized using 26.5 g of sodium meta-bisulfite. The aqueous layer is then decanted and the reaction mixture washed two more times with 200-ml increments of water. Residual acid is neutralized with sodium bicarbonate. The remaining solids are then filtered and dried. The resulting white solids are analyzed using liquid chromatography. The product contains 97.08 area percent decabromodiphenyl oxide.

It may be seen from the preceding example that the process of the present invention is capable of producing very high purity decabromodiphenyl oxide in high yield by advantageously employing only a slight excess of bromine and a very low addition temperature.

As previously mentioned, the preceding example serves only to illustrate the invention and its advantages, and it should not be interpreted as limiting since further modifications of the disclosed invention will be apparent to those skilled in the art. All such modifications are deemed to be within the scope of the invention as defined by the following claims.

What is claimed is:

1. A process for the preparation of perbrominated aromatic compounds comprising adding an aromatic compound to a brominating agent in methylene chloride in the presence of a catalyst at a temperature of about 15° C. or lower and then raising the temperature of the resulting mixture to an elevated temperature in order to achieve substantial perbromination of the aromatic compound.

2. The process of claim 1 wherein the aromatic compound is diphenyl oxide and the brominating agent is bromine.

3. The process of claim 2 wherein the amount of bromine employed is from about 0 to about 25 percent in excess of the stoichiometric amount.

4. The process of claim 3, wherein the catalyst is aluminum chloride or aluminum bromine.

5. The process of claim 4 wherein the temperature is about 10° C. or less.

6. The process of claim 5 wherein the catalyst is aluminum chloride.

7. The process of claim 6 wherein the addition temperature is from about 5° C. to about −15° C.

8. The process of claim 1 wherein the catalyst is employed in solid lump form.

9. A process for substantially perbrominating diphenyl oxide comprising the steps:
   (a) adding the diphenyl oxide at an addition temperature of about 15° C. or lower to a mixture comprising:
      (1) methylene chloride;
      (2) a catalyst; and
      (3) an amount of bromine which is from about 0 to about 25 percent in excess of the stoichiometric amount; and then
   (b) continuing the reaction at an elevated temperature, at which reflux may occur, after addition of the diphenyl oxide has been completed in order to achieve substantial perbromination of the diphenyl oxide.

10. The process of claim 9 wherein the catalyst is employed in a solid lump form.

11. The process of claim 10 wherein the addition temperature is about 10° C. or less.

12. The process of claim 10 wherein the addition temperature is from about 5° C. to about −15° C.

13. The process of claim 10 wherein the catalyst is aluminum chloride.

14. The process of claim 10 wherein the amount of bromine is from about 5 to about 15 percent in excess of the stoichiometric amount.

15. A process for the preparation of decabromodiphenyl oxide comprising adding an aromatic compound selected from the group consisting of diphenyl oxide, partially brominated diphenyl oxides, and mixtures thereof, to an amount of bromine, which is from about 5 to about 15 percent in excess of the stoichiometric amount, in methylene chloride in the presence of a bromination catalyst at an addition temperature of about 10° C. or lower and then raising the temperature of the resulting mixture to an elevated temperature.

16. The process of claim 15 wherein the catalyst is aluminum chloride.

17. The process of claim 15 wherein the catalyst is a non-metal catalyst and is employed in an agglomerated form.

* * * * *

UNITED STATES PATENT AND TRADEMARK OFFICE
CERTIFICATE OF CORRECTION

PATENT NO. : 4,521,633

DATED : June 4, 1985

INVENTOR(S) : Joseph J. Pedjac

It is certified that error appears in the above-identified patent and that said Letters Patent is hereby corrected as shown below:

Column 2, line 48, "bromine" should read
-- bromide --.

Column 5, Claim 4, lines 41 and 42, "claim 3,"
should read -- claim 3 -- and
"aluminum bromine" should read -- aluminum bromide --.

Signed and Sealed this

Twenty-ninth Day of October 1985

[SEAL]

Attest:

DONALD J. QUIGG

Attesting Officer

Commissioner of Patents and
Trademarks—Designate